United States Patent [19]

Benoit et al.

[11] Patent Number: 5,053,390

[45] Date of Patent: Oct. 1, 1991

[54] NOVEL INSECTICIDAL METHOD

[75] Inventors: Marc Benoit, Roquevaire; Jean-Pierre Demoute, Auriol, both of France

[73] Assignee: Roussel Uclaf, Paris, France

[21] Appl. No.: 563,490

[22] Filed: Aug. 7, 1990

[30] Foreign Application Priority Data

Aug. 8, 1989 [FR] France .................................. 8910649

[51] Int. Cl.5 ...................... A01N 37/08; A01N 37/34; A01N 43/08; A01N 57/00
[52] U.S. Cl. ........................................ 574/7; 514/119; 514/461; 514/521; 514/530; 514/531
[58] Field of Search ..................................... 514/7, 119

[56] References Cited

U.S. PATENT DOCUMENTS

| | | | |
|---|---|---|---|
| 3,832,394 | 8/1974 | Niida et al. | 71/86 |
| 4,100,275 | 7/1978 | Ratcliffe et al. | 514/119 |
| 4,309,208 | 11/1978 | Takematsu et al. | 71/86 |
| 4,448,601 | 5/1984 | Takematsu et al. | 71/86 |
| 4,455,163 | 6/1984 | Takematsu et al. | 71/86 |
| 4,552,584 | 11/1985 | Takematsu et al. | 71/86 |
| 4,622,060 | 11/1986 | Takematsu et al. | 71/86 |

FOREIGN PATENT DOCUMENTS 0002039  5/1979  European Pat. Off. ............ 514/119

Primary Examiner—Allen J. Robinson
Attorney, Agent, or Firm—Bierman and Muserlian

[57] ABSTRACT

A method of combatting insects comprising contacting insects with an insecticidally effective amount of L-2-amino-4-[(hydroxy) (methyl) phosphinyl]-butyryl-L-alanyl-L-alanine.

6 Claims, No Drawings

NOVEL INSECTICIDAL METHOD

STATE OF THE ART

L-2-amino-4-[(hydroxy) (methyl) phosphinyl]-butyryl-L-alanyl-L-alainine or bialaphos is disclosed in French Patent No. 2,147,291 and U.S. Pat. Nos. 4,455,163; 4,448,601; 4,552,584; 4,622,060 and 4,309,208 as a herbicide and is sold commerically under the name Herbiace. Other pertinent prior art includes Chemical Patents Index, Basic Abstracts Journal, Vol. 26, No. 45565, Patents Abstracts of Japan, Vol. II, No. 349 and Chem. Abs., Vol. 107, No. 21, p. 289, No. 193,081m.

OBJECTS OF THE INVENTION

It is an object of the invention to provide a novel insecticidal method.

This and other objects and advantages of the invention will become obvious from the following detailed description.

THE INVENTION

The novel method of the invention of combatting insects comprises contacting insects with an insecticidally effective amount of L-2-amino-4-[(hydroxy) (methyl) phosphinyl]-butyryl-L-alanyl-L-alanine.

The method is useful for combatting parasitic insects of vegetation, of premises and warm-blooded animals and can therefore be used especially for combatting insects in the agricultural field such as lice, larvae of lepidoptera and coleoptera.

The method of the invention can also be used for combatting insects in premises, notably for combatting flies, mosquitoes and cockroaches and for combatting parasitic insects of animals such as fleas and lice.

The compositions of the invention may be prepared by the usual processes of the agro- chemical industry, or of the veterinary industry or of the industry of products intended for animal nutrition. These may be in the form of powders, granules, suspensions, emulsions, aerosol solutions, combustible strips, baits or other preparations normally employed for the use of such compounds. When combatting parasites of animals, the compositions of the invention can be used in the form of a spray, a bath or by the "pour-on" method.

The insecticidal compositions may be in the form of solutions of 0.01 to 20 g/l, preferably 0.1 to 10 g/l and most preferably 0.5 to 5 g/l, of bialaphos. When used to combat parasitic insects of animals and vegetation, they may be used at 1 to 20, preferably 2 to 6 g/hectoliter of solution of bialaphos. When used for treating crops, the compositions are used at a dose of 1 to 1,000 g/hectare of bialaphos.

The method is useful for combatting lepidoptera, particularly Spodoptera and insects resistant to pyrethrinoids.

In a modification of the method of the invention, bialaphos may be used in combination with at least one pyrethrinoid ester selected from the group consisting of the esters of allethrolone, of 3,4,5,6-tetrahydrophthalimidomethyl alcohol, of 5-benzyl-3-furyl methyl alcohol, of 3-phenoxybenzyl alcohol and of -cyano-3-phenoxy benzyl alcohols with chrysanthemic acids, by the esters of 5-benzyl-3-furyl methyl alcohol with 2,2-dimethyl-3-(2-oxo-3,4,5,6-tetrahydrothiophenylidenemethyl)-cyclopropane-1-carbosylic acids, by the esters of 3-phenoxybenzyl alcohol and of o-cyano-3-phenoxybenzyl alcohols with 2,2-dimethyl-3-(2,2-dichlorovinyl)-cyclopropane-1-carboxylic acids, by the esters of α-cyano-3-phenoxy-benzyl alcohols with 2,2-dimethyl-3-(2,2-dibromovinyl)-cyclopropane-1-carboxylic acids, by the esters of 3-phenoxybenzyl alcohol with 2-parachlorophenyl-2-isopropyl acetic acids, by the esters of allethrolones, of 3,4,5,6-tetrahydrophthalimidomethyl alcohol, of 5-benzyl-3-furyl methyl alcohol, of 3-phenoxybenzyl alcohol, and of α-cyano-3-phenoxybenzyl alcohols with 2,2-dimethyl-3-(1,2,2,2-tetrahaloethyl)-cycyopropane-1-carboxylic acids, in which "halo" represents a fluorine, chlorine or bromine atom, it being understood that the acid and alcohol copulas of the above pyrethrinoid esters can exist in all their possible stereoisomer forms.

In the following examples there are described several preferred embodiments of the invention. However, it should be understood that the invention is not intended to be limited to the specific embodiments.

EXAMPLE 1

Insecticidal compositions were prepared as solutions of 1 g or 0.5 g/l of bialaphos.

EXAMPLE 2

*Study of the lethal effect on larvae of Spodootera Littoralis*

The tests were carried out by topical application of a microliter of an acetone solution using an Arnold micromanipulator on the dorsal thorax of the larvae. 15 larvae were used per dose of product under test and the larvae used were fourth-stage larvae that is about 10 days old when they are bred at 24° C. and 65% relative humidity. After treatment, the individual larvae were placed on an artificial nutritive medium (Poitout medium) and the mortality check was carried out.

A) The experimental results obtained are summarized in the following table:

| Doses g/l | % mortality at | | | | |
| --- | --- | --- | --- | --- | --- |
| | day 1 | day 2 | day 3 | day 4 | day 5 |
| 10 | 13 | 100 | 100 | 100 | 100 |
| 1 | 0 | 100 | 100 | 100 | 100 |
| 0.1 | 0 | 7 | 10 | 37 | 70 |
| 0.01 | 3 | 7 | 7 | 7 | 20 |
| Control | 0 | 7 | 13 | 13 | 13 |

B) The same test as in paragraph A was repeated with a strain of Spodoptera Littoralis strongly resistant to deltamethrine (on which 10 g/l. of deltamethrine only caused a partial mortality). The results obtained are the following:

| Doses g/l | % mortality at | | | |
| --- | --- | --- | --- | --- |
| | day 1 | day 2 | day 3 | day 4 |
| 10 | 37 | 63 | 100 | 100 |
| 1 | 3 | 10 | 83 | 93 |
| 0.1 | 10 | 17 | 23 | 43 |

It is noted that there is almost no difference in the activity of the product between the sensitive strain and the resistant strain of Spodoptera Littoralis.

Various modifications of the method of the invention may be made without departing from the spirit or scope thereof and it is to be understood that the invention is to be limited only as defined in the appended claims.

What is claimed is:

1. A method of combatting insects comprising contacting insects with an insecticidally effective amount of L-2-amino-4-[(hydroxy) (methyl) phosyhinyl]-butyryl-L-alanyl-L-alanine.

2. The method of claim 1 wherein the contact is effected with a solution containing 0.01 to 20 g/l of the active ingredient.

3. The method of claim 2 containing 0.1 to 10 g/l of the active ingredient.

4. The method of claim 2 containing 0.5 to 5 g/l of the active ingredient.

5. The method of claim 1 wherein the insects are lepidoptera.

6. The method of claim 1 wherein there is also present an insecticidally effective amount of at least one member of the group consisting of the esters of allethrolone, of 3,4,5,6-tetrahydrophthalinido-methyl alcohol, of 5-benzyl-3-furyl methyl alcohol with 2,2-dimethyl-3-(2-oxo-3,4,5,6-tetrahydrothiophenylidenemethyl) -cyclopropane-1-carboxylic acids, by the esters of 3-phenoxybenzyl alcohol and of α-cyano-3-phenoxybenzyl alcohols with 2,2-dimethyl-3-(2,2-dichlorovinyl)-cyclopropane-1-carboxylic acids, by the esters of α-cyano-3-phenoxybenzyl alcohols with 2,2-dimethyl-3-(2,2-dibromovinyl)-cyclopropane-1-carboxylic acids, by the esters of 3-phenoxybenzyl alcohol with 2-para-chlorophenyl-2-isopropyl acetic acids, by the esters of allethrolones, of 3,4,5,6-tetrahydrophthalimidomethyl alcohol, and of α-cyano-3-phenoxybenzyl alcohols with 2,2-dimethyl-3-(1,2,2,2-tetrahaloethyl)-cyclopropane-1-carboxylic acids, in which "halo" represents a fluorine, chlorine or bromine atom, it being understood that the acid and alcohol copulas of the above pyrethrinoid esters can exist in all their possible stereoisomer forms.

* * * * *